United States Patent [19]

Seki et al.

[11] 4,076,814
[45] Feb. 28, 1978

[54] PREVENTIVE AND CURATIVE COMPOSITIONS AGAINST MYCOPLASMOSIS

[75] Inventors: Isao Seki; Noritoshi Kitano; Fusao Kondo, all of Tokyo, Japan

[73] Assignee: Sankyo Company Limited, Tokyo, Japan

[21] Appl. No.: 690,863

[22] Filed: May 28, 1976

[30] Foreign Application Priority Data

Jun. 9, 1975 Japan .................................. 50-69324
Oct. 1, 1975 Japan .................................. 50-118580

[51] Int. Cl.$^2$ ..................... A61K 31/535; A61K 31/54
[52] U.S. Cl. ................................. 424/248.5; 424/246; 424/248.51
[58] Field of Search .................. 424/248.5, 246, 248.51

[56] References Cited

PUBLICATIONS

Kasugai et al. - Chem. Abst., vol. 80 (1974) p. 44679j.
Chem. Abst. 8th Cumulative Index (1967–1971) p. 19775s.

*Primary Examiner*—Sam Rosen
*Attorney, Agent, or Firm*—Flynn & Frishauf

[57] ABSTRACT

Use of dithiocarbamic acid derivatives having the structure

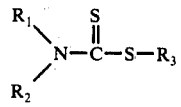

in which $R_1$, $R_2$ and $R_3$ are various organic radicals as preventive and curative agents against mycoplasmosis. These derivatives are prepared from the starting materials having the structure

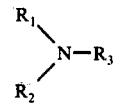

by reaction with carbon disulfide or from the starting materials having the structure

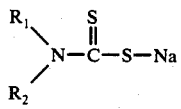

by reaction with $R_3$-halide.

12 Claims, No Drawings

PREVENTIVE AND CURATIVE COMPOSITIONS AGAINST MYCOPLASMOSIS

This invention relates to a new use of certain dithiocarbamic acid derivatives as preventive and curative agents against mycoplasmosis.

More particularly, it is concerned with a preventive and curative composition against mycoplasmosis which comprises as an active ingredient a dithiocarbamic acid derivative of the formula

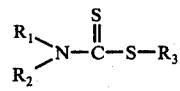
(I)

wherein $R_1$ and $R_2$ may be the same or different and each represents an alkyl group of 1 to 4 carbon atoms, cyclohexyl group or an aralkyl group having 6 or 10 carbon atoms in the aryl moiety and 1 to 3 carbon atoms in the alkyl moiety or they may, jointly with the nitrogen atom to which they are attached, form a 5–7 membered heteroalicyclic ring which may further contain as another hetero atom one of nitrogen atom and oxygen atom other than the nitrogen atom linked with $R_1$ and $R_2$ and may have as substituent an alkyl group of 1 to 4 carbon atoms, carboxyl group or a carboxylic acid ester group; and $R_3$ is a group —$CH_2$—$R_4$ in which $R_4$ is a 5–7 membered 2-oxocycloalkyl group optionally substituted with 1–3 $C_1$–$C_4$ alkyl groups;

a group

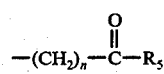

in which $n$ is an integer of 1 or 2 and $R_5$ is naphthyl group, a phenyl group optionally substituted with 1–2 groups selected from the group consisting of hydroxy, $C_1$–$C_{12}$ alkyl, $C_1$–$C_4$ alkoxy, nitro and halogen or a 5–7 membered heterocyclic group which has as hetero atom 1 or 2 atoms of oxygen atom, nitrogen atom and sulfur atoms and may be substituted with 1–3 groups selected from the group consisting of $C_1$–$C_4$ alkyl, hydroxy, hydroxymethyl, halogenomethyl, dihalogenomethyl, trihalogenomethyl, nitro and halogen;

a group

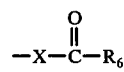

in which $R_6$ is an alkyl group of 1 to 12 carbon atoms, a 5–6 membered cycloalkyl group, an aralkyl group which has 6 or 10 carbon atoms in the aryl moiety and 1 to 4 carbon atoms in the alkyl moiety and may be substituted with $C_1$–$C_4$ alkyl, hydroxy, nitro, $C_1$–$C_4$ alkoxy or halogen or an alkenyl group of 2 to 5 carbon atoms which may be substituted with cycloalkenyl or phenyl, said phenyl being optionally substituted with $C_1$–$C_4$ alkyl, hydroxy, nitro, $C_1$–$C_4$ alkoxy or halogen and X is a group

wherein $R_7$ is hydrogen, $C_1$–$C_{12}$ alkyl, cyclohexyl, aralkyl of $C_6$ or $C_{10}$ in the aryl moiety and $C_1$–$C_4$ in the alkyl moiety, $C_2$–$C_4$ alkenyl, $C_2$–$C_3$ alkynyl or phenyl or a group

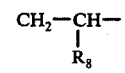

wherein $R_8$ is hydrogen, $C_1$–$C_{12}$ alkyl, cyclohexyl, aralkyl of $C_6$ or $C_{10}$ in the aryl moiety and $C_1$–$C_4$ in the alkyl moiety, said aryl moiety being optionally substituted with $C_1$–$C_4$ alkyl, hydroxy, $C_1$–$C_4$ alkoxy or halogen, or phenyl optionally substituted with $C_2$–$C_4$ alkyl, hydroxy, $C_1$–$C_4$ alkoxy or halogen; or a group

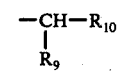

in which $R_9$ is hydrogen atom, an alkyl group of 1 to 4 carbon atoms, cyclohexyl group or phenyl group and $R_{10}$ is a phenyl group which has one hydroxy group at the o- or p-position and 2–4 groups selected from the group consisting of $C_1$–$C_4$ alkyl, halogen, $C_1$–$C_4$ alkoxy, $C_2$–$C_4$ alkenyl hydroxyalkyl of $C_1$–$C_4$, a group

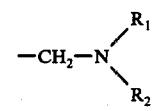

wherein $R_1$ and $R_2$ are as defined above and a group

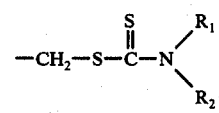

wherein $R_1$ and $R_2$ are as defined above, a naphthyl group which has one hydroxy group at the 1- or 2-position and optionally halogen or a group

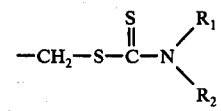

wherein $R_1$ and $R_2$ are as defined above, a group

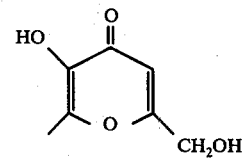

or a group

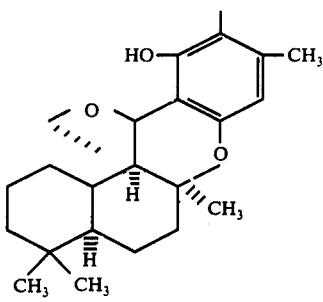

or a pharmaceutically acceptable salt thereof.

In the above formula (I), $R_1$ and $R_2$ may be exemplified by methyl, ethyl, n-propyl, isopropyl, n-butyl, isobutyl, tert-butyl, cyclohexyl, benzyl, phenethyl, phenylpropyl, morpholino, piperidino, pyrrolidino, hexamethyleneimino, 3-oxazolidino, 4-methyl-1-piperazino, 2-methoxycarbonyl-1-pyrrolidino, 2-benzyloxycarbonyl-1-pyrrolidino, 2-carboxy-1-pyrrolidino. With respect to the definition of $R_3$, $R_4$ represents a 5–7 membered 2-oxocycloalkyl group unsubstituted or substituted with 1–3 lower alkyl groups such as methyl, ethyl, propyl and butyl. $R_5$ represents a naphthyl group, a phenyl group unsubstituted or substituted with 1 or 2 groups selected from the group consisting of an alkyl group such as methyl, ethyl, propyl, butyl, pentyl, hexyl, heptyl, octyl, dodecyl, etc., alkoxy group such as methoxy, ethoxy, propoxy, butoxy, etc., hydroxy group, nitro group and a halogen atom, or a 5–7 membered monovalent heterocyclic group having as ring members 1 or 2 (the same or different) atoms of oxygen, nitrogen and sulfur, said heterocyclic group being unsubstituted or substituted with 1–3 groups selected from the group consisting of a lower alkyl group such as methyl, ethyl, propyl, butyl, etc., hydroxy group, hydroxymethyl group, a halogenomethyl group, a dihalogenomethyl group, a trihalogenomethyl group, nitro group and a halogen atom. $R_6$ represents a straight-chain or branched alkyl group such as methyl, ethyl, propyl, isopropyl, butyl, tert-butyl, hexyl, 3-methylhexyl, octyl, tert-octyl, undecyl, ect.; a 5–6 membered cycloalkyl group; an aralkyl group (in which the aryl may be unsubstituted or substituted with an alkyl group, hydroxy group, nitro group, an alkoxy group or a halogen atom) such as benzyl, phenethyl, o-, m-, p-nitrobenzyl, o-, m-, p-hydroxyphenethyl, o-, m-, p-methylphenethyl, o-, m-, p-methoxyphenethyl, o-, m-, p-chlorophenethyl, o-, m-, p-nitrophenethyl, etc.; an alkenyl group (which may be unsubstituted or substituted with a cycloalkenyl group or with an unsubstituted or substituted phenyl group, the substituent of which is an alkyl group, hydroxy group, nitro group, an alkoxy group or a halogen atom) such as 1-propenyl, allyl, styryl, 1,3-pentadienyl, o-, m-, p-hydroxystyryl, o-, m-, p-methylstyryl, o-, m-, p-methoxystyryl, o-, m-, p-chlorostyryl, o-, m-, p-nitrostyryl, 2-(2,6,6-trimethyl-1-cyclohexenyl)-vinyl. X represents a group

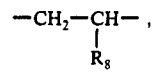

or a group

wherein $R_7$ represents a hydrogen atom; a straight-chain or branched alkyl group such as methyl, ethyl, propyl, isopropyl, butyl, octyl, decyl, etc.; cyclohexyl group; an aralkyl group such as benzyl, phenethyl, etc.; an alkenyl group as vinyl, allyl, 1-butenyl, 2-butenyl, etc.; an alkynyl group such as 1-propynyl, 2-propynyl, etc., and $R_8$ represents a hydrogen atom; a straight-chain or branched alkyl group such as methyl, ethyl, isopropyl, butyl, pentyl, 2-methylpentyl, decyl, etc.; cyclohexyl group; an aralkyl group (in which the aryl may be unsubstituted or substituted with an alkyl group, hydroxy group, an alkoxy group or a halogen atom) such as benzyl, phenethyl, o-, m-, p-hydroxybenzyl, o-, m-, p-methylbenzyl, o-, m-, p-methoxybenzyl, o-, m-, o-chlorobenzyl, etc.; an unsubstituted or substituted phenyl group (as the substituents may be mentioned an alkyl group, hydroxy group, an alkoxy group or a halogen atom) such as phenyl, o-, m-, p-tolyl, o-, m-, p-hydroxyphenyl, o-, m-, p-methoxyphenyl, o-, m-, p-chlorophenyl, etc. $R_9$ represents hydrogen atom, an alkyl group such as methyl, ethyl, propyl, isopropyl, butyl, tert-butyl, cyclohexyl group or phenyl group. $R_{10}$ may be exemplified by 4-hydroxy-3,5-dimethylphenyl, 4-hydroxy-2-isopropyl-5-methylphenyl, 4-hydroxy-3-tert-butyl-5-methylphenyl, 4-hydroxy-3,5-di-tert-butylphenyl, 4-hydroxy-3,5-diisopropylphenyl, 2-hydroxy-3,5-dimethylphenyl, 2-hydroxy-3,5-di-tert-butylphenyl, 4-hydroxy-3,5-dimethoxyphenyl, 4-hydroxy-3,5-dichlorophenyl, 4-hydroxy-3-dimethylaminomethyl-5-methylphenyl, 4-hydroxy-3-(4-methyl-1-piperazinomethyl)-5-methylphenyl, 4-hydroxy-3-dimethylaminomethyl-5-n-propylphenyl, 4-hydroxy-3-dimethylaminomethyl-5-sec.-butylphenyl, 2-hydroxy-3-methoxy-5-hydroxymethylphenyl, 2-hydroxy-3-methoxy-5-propenylphenyl, 4-hydroxy-5-dimethylamino-thiocarbamoylthiomethyl-2-methylphenyl, 4-hydroxy-5-dimethylaminothiocarbamoylthiomethyl-3-tert-butylphenyl, 4-hydroxy-5-(4-methyl-1-piperazinothiocarbonylthiomethyl)-3-n-propylphenyl, 2-hydroxy-5-(1-piperidinothiocarbonylthiomethyl)-3-tert-butylphenyl, 2-hydroxy-5-(4-methyl-1-piperazinothiocarbonylthiomethyl)-3-tert-butylphenyl, 4-chloro-1-hydroxy-2-naphthyl, 4-dimethylaminothiocarbamoylthiomethyl-1-hydroxy-2-naphthyl, 2-hydroxy-1-naphthyl, 4-morpholinothiocarbonylthiomethyl-2-hydroxy-1-naphthyl, 5-hydroxy-2-hydroxymethyl-4-oxo-4H-pyran-6-yl or a group of formula

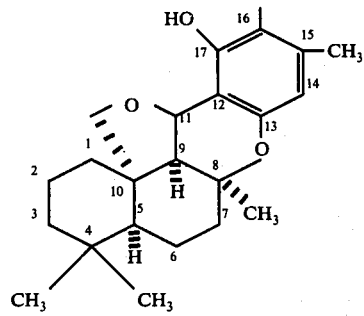

As the salts of the derivatives of dithiocarbamic acid represented by the formula (I), there are mentioned acid addition salts of the amine group and alkali or alkaline earth metal salts of the carboxyl group. As the acid addition salt of the amine group, there may be mentioned such pharmaceutically acceptable non-toxic salts are those with hydrochloric acid, sulfuric acid, oxalic acid, maleic acid, tartaric acid, malonic acid, citric acid, phthalic acid or naphthalene-disulfonic acid and the like. As the alkali or alkaline earth metal salts of the carboxyl group, there may be mentioned pharmaceutically acceptable non-toxic salts as those of, for example, lithium, sodium, potassium, magnesium, calcium and the like.

Mycoplasmosis is a disease of poultry and domestic animals caused by mycoplasma or a group of microorganisms belonging to PPLO (Pleuro-pneumonia-like organisms). Frequently pigs, chickens and turkeys suffer from this disease, which causes chronic respiratory disorder or arthritis and causes heavy damage on poultry and stock breeding industry. Mycoplasma-infected disease affects poultry in particular, and causes the stoppage of egg-laying and extreme fall of fertilization ratio or hatching ratio. This disease further causes fatal damage such as the decrease of the body weight of a chicken for broiler.

An outbreak of these symptoms caused by this disease shows a tendency to increase year by year. The symptoms caused by the infection (mixed-infection) show complicated aspect.

It was reportedly observed that mycoplasma is sensitive in vitro to antibiotics such as tetracycline, macrolide, aminoglyco-side and the like. Recently, tylosin, an antibiotic belonging to macrolide came to be applied as a preventive and curative agent against this disease. But, in spite of the various studies on the chemotherapy by antibiotics or antibacterial pharmaceuticals, the perfect extinguishment of mycoplasma from the interior of animal body can hardly be accomplished.

As a result of our research to develop a more effective preventive and curvative agent against mycoplasmosis, it has been found that the dithiocarbamic acid derivatives (I) or salts thereof show a strong inhibition against various kinds of mycoplasmosis in an extremely low concentration.

It is, accordingly, a primary object of this invention to provide a new and more effective preventive and curvative composition against mycoplasmosis which comprises as an active ingredient the dithiocarbamic acid derivative (I) or a salt thereof.

Other subjects and advantages of this invention will be apparent from the following description.

Of the dithiocarbamic acid derivatives (I) which may be effectively employed in the present composition, there can be mentioned, as a preferable group in view of a biological activity, those derivatives of the formula (I) wherein $R_1$ and $R_2$ individually represent an alkyl group of 1 to 4 carbon atoms, cyclohexyl group or benzyl group or they may, jointly with the nitrogen atom to which they are attached, form a 5-7 membered heteroalicyclic ring which may further contain as another hetero atom one of nitrogen atom and oxygen atom other than the nitrogen atom linked with $R_1$ and $R_2$ and may have as substituent an alkyl group of 1 to 4 carbon atoms: and $R_4$ is a 5-6 membered 2-oxocycloalkyl group optionally substituted with 1-2 $C_1$-$C_4$ alkyl groups;

$n$ is 2 and $R_5$ is naphthyl group, a phenyl group optionally substituted with 1-2 groups selected from the group consisting of hydroxy, $C_1$-$C_8$ alkyl, nitro and halogen or a 5-6 membered heterocyclic group which has as hetero atom 1 to 2 atoms of oxygen atom and nitrogen atom;

$R_6$ is an alkyl group of 1 to 12 carbon atoms, a phenethyl group which may be substituted with methyl, hydroxy, methoxy or halogen, an alkenyl group of 3 carbon atoms or a styryl group which may be substituted with methyl, hydroxy, methoxy or halogen and X is a group

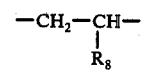

wherein $R_8$ is hydrogen, $C_1$-$C_{12}$ alkyl, cyclohexyl, benzyl optionally substituted with methyl, hydroxy or methoxy or phenyl; or $R_9$ is hydrogen atom, methyl group cyclohexyl group or phenyl group and $R_{10}$ is a phenyl group which has one hydroxy group at the o- or p-position and 2-4 groups selected from the group consisting of $C_1$-$C_4$ alkyl, chlorine, methoxy, propenyl, hydroxymethyl, a group

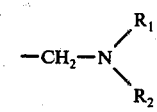

wherein $R_1$ and $R_2$ are as defined above and a group

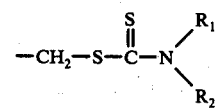

wherein $R_1$ and $R_2$ are as defined above, naphthyl group, a group

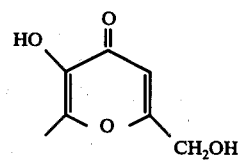

or a group

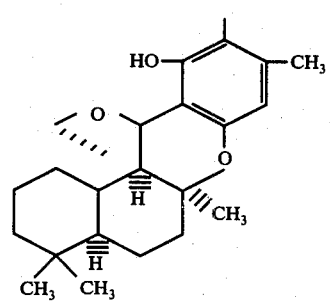

Moreover, the most preferable group of the dithiocarbamic acid derivatives (I) includes those derivatives of the formula (I) wherein R₁ and R₂ individually represent an alkyl group of 1 to 4 carbon atoms or benzyl group or they may, jointly with the nitrogen atom to which they are attached, form a 6-7 membered heteroalicyclic ring which may further contain as another hetero atom one of nitrogen atom and oxygen atom other than the nitrogen atom linked with R₁ and R₂ and may be substituted with methyl; and R₄ is a 5-6 membered 2-oxocycloalkyl group;

n is 2 and R₅ is naphthyl group, a phenyl group optionally substituted with 1-2 groups selected from the group consisting of hydroxy, C₁-C₈ alkyl, nitro and chlorine or a 5-6 membered heterocyclic group which has as hetero atom one of oxygen atom and nitrogen atom;

R₆ is alkyl group of 1 to 12 carbon atoms, a phenethyl group which may be substituted with methyl, hydroxy or methoxy or a styryl group which may be substituted with methyl, hydroxy or methoxy and X is a group

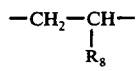

wherein R₈ is hydrogen, C₁-C₁₂ alkyl or phenyl; or R₉ is hydrogen atom or phenyl group and R₁₀ is a phenyl group which has one hydroxy group at the o- or p-position and 2-4 groups selected from the group consisting of C₁-C₄ alkyl, hydroxymethyl, a group

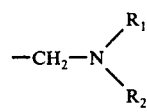

wherein R₁ and R₂ are as defined above and a group

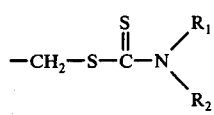

wherein R₁ and R₂ are as defined above, a group

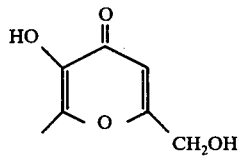

or a group

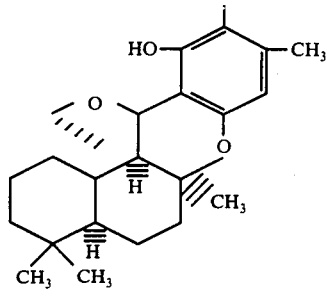

Representatives of the dithiocarbamic acid derivatives (I) in this invention are illustratively shown herinbelow. The Compound Nos. for designation of particular compounds frequently referred to hereinafter.

1. 2-Oxocyclopentylmethyl dimethyldithiocarbamate
2. 2-Oxocyclopentylmethyl diethyldithiocarbamate
3. 2-Oxocyclopentylmethyl 4-morpholinecarbodithioate
4. 2-Oxocyclopentylmethyl 1-piperidinecarbodthioate
5. 2-Oxocyclohexylmethyl dimethyldithiocarbamate
6. 2-Oxocyclohexylmethyl diethyldithiocarbamate
7. 2-Oxocyclohexylmethyl n-butylmethyldithiocarbamate
8. 2-Oxocyclohexylmethyl 1-pyrrolidinecarbodithioate
9. 2-Oxocyclohexylmethyl 1-piperidinecarbodithioate
10. 2-Oxocyclohexylmethyl 1-hexamethyleneiminecarbodithioate
11. 2-Oxocyclohexylmethyl 3-oxazolidinecarbodithioate
12. 2-Oxocyclohexylmethyl 4-morpholinecarbodithioate
13. 2-Oxocyclohexylmethyl 4-methyl-1-piperazinecarbodithioate
14. 2-Methyl-6-oxocyclohexylmethyl diethyldithiocarbamate
15. 2,2-Dimethyl-6-oxocyclohexylmethyl dimethyldithiocarbamate
16. 2,4,4-Trimethyl-6-oxocyclohexylmethyl dimethyldithiocarbamate
17. 2,4,4-Trimethyl-6-oxocyclohexylmethyl 1-piperidinecarbodithioate
18. 2,4,4-Trimethyl-6-oxocyclohexylmethyl 4-morpholinecarbodithioate
19. 3-Isopropyl-6-methyl-2-oxocyclohexylmethyl dimethyldithiocarbamate
20. 2-Oxocycloheptylmethyl diethyldithiocarbamate
21. Phenacyl dimethyldithiocarbamate
22. Phenacyl diethyldithiocarbamate
23. 2-Benzoylethyl dimethyldithiocarbamate
24. 2-Benzoylethyl diethyldithiocarbamate
25. 2-Benzoylethyl n-butylmethyldithiocarbamate
26. 2-Benzoylethyl cyclohexylmethyldithiocarbamate
27. 2-Benzoylethyl benzylmethyldithiocarbamate
28. 2-Benzoylethyl phenethylmethyldithiocarbamate
29. 2-Benzoylethyl 2-pyrrolidinecarbodithioate
30. 2-Benzoylethyl 1-piperidinecarbodithioate
31. 2-Benzoylethyl 1-hexamethyleneiminecarbodithioate
32. 2-Benzoylethyl 3-oxazolidinecarbodithioate
33. 2-Benzoylethyl 4-morpholinecarbodithioate 34. 2-Benzoylethyl 4-methyl-1-piperazinecarbodithioate hydrochloride
35. 2-Benzoylethyl L-2-methoxycarbonyl-1-pyrrolidinecarbodithioate
36. 2-Benzoylethyl L-2-benzyloxycarbonyl-1-pyrrolidinecarbodithioate
37. Sodium salt of 2-benzoylethyl L-2-carboxy-1-pyrrolidinecarbodithioate
38. 2-(β-naphthoyl)ethyl dimethyldithiocarbamate
39. 2-(α-naphthoyl)ethyl dimethyldithiocarbamate
40. 2-(o-Hydroxybenzoyl)ethyl dimethyldithiocarbamate
41. 2-(o-Hydroxybenzoyl)ethyl 1-piperidinecarbodithioate
42. 2-(o-Hydroxybenzoyl)ethyl 4-morpholinecarbodithioate
43. 2-(o-Hydroxybenzoyl)ethyl 4-methyl-1-piperazinecarbodithioate
44. 2-(p-Hydroxybenzoyl)ethyl diethyldithiocarbamate
45. 2-(p-Hydroxybenzoyl)ethyl 4-morpholinecarbodithioate
46. 2-(p-Methoxybenzoyl)ethyl dimethyldithiocarbamate
47. 2-(p-Methoxybenzoyl)ethyl 1-pyrrolidinecarbodithioate
48. 2-(p-Methoxybenzoyl)ethyl 4-morpholinecarbodithioate
49. 2-(p-Chlorobenzoyl)ethyl 4-morpholinecarbodithioate
50. 2-(p-Bromobenzoyl)ethyl dimethyldithiocarbamate
51. 2-(p-Bromobenzoyl)ethyl 4-morpholinecarbodithioate
52. 2-(3,4-Dichlorobenzoyl)ethyl dimethyldithiocarbamate
53. 2-(3,4-Dichlorobenzoyl)ethyl 1-piperidinecarbodithioate
54. 2-(3,4-Dichlorobenzoyl)ethyl b 4-morpholinecarbodithioate
55. 2-(p-Toluoyl)ethyl dimethyldithiocarbamate
56. 2-(m-Toluoyl)ethyl dimethyldithiocarbamate
57. 2-(o-Toluoyl)ethyl dimethyldithiocarbamate 58. 2-(p-n-Octylbenzoyl)ethyl dimethyldithiocarbamate
59. 2-(o-Nitrobenzoyl)ethyl dimethyldithiocarbamate
60. 2-(o-Nitrobenzoyl)ethyl 4-methyl-1-piperazinecarbodithioate
61. 2-(o-Nitrobenzoyl)ethyl 4-morpholinecarbodithioate
62. 2-(m-Nitrobenzoyl)ethyl 1-piperidinecarbodithioate
63. 2-(m-Nitrobenzoyl)ethyl 4-morpholinecarbodithioate
64. 2-(p-Nitrobenzoyl)ethyl 4-morpholinecarbodithioate
65. 2-(2-Furoyl)ethyl dimethyldithiocarbamate
66. 2-(2-Furoyl)ethyl 4-methyl-1-piperazinecarbodithioate
67. 2-(2-Furoyl)ethyl 4-morpholinecarbodithioate
68. 2-(2-Thenoyl)ethyl 4-morpholinecarbodithioate
69. 2-Nicotinoyl dimethyldithiocarbamate
70. 2-Nicotinoylethyl 4-methyl-1-piperazinecarbodithioate
71. 2(2-Chloromethyl-5-nitronicotinoyl)ethyl dimethyldithiocarbamate
72. 2(2-Dichloromethyl-5-nitronicotinoyl)ethyl dimethyldithiocarbamate
73. 2-(6-Trichloromethyl-2-methyl-5-nitronicotinoyl)ethyl dimethyldithiocarbamate
74. 2-(5-Thiazolcarbonyl)ethyl dimethyldithiocarbamate
75. 2-(1-Methyl-5-imidazolcarbonyl)ethyl 4-methyl-1-piperazinecarbodithioate
76. 2-(5-Pyrimidinecarbonyl)ethyl dimethyldithiocarbamate
77. 2-(5-Pyridazinecarbonyl)ethyl dimethyldithiocarbamate
78. 2-Acetylethyl dimethyldithiocarbamate
79. 2-Acetylethyl diethyldithiocarbamate
80. 2-Acethylethyl butylmethyldithiocarbamate
81. 2-Acetylethyl cyclohexylmethyldithiocarbamate
82. 2-Acetylethyl benzylmethyldithiocarbamate
83. 2-Acetylethyl 1-pyrrolidinecarbodithioate
84. 2-Acetylethyl 2-carboxy-1-pyrrolidinecarbodithioate
85. Sodium salt of 2-acetylethyl 2-carboxy1-pyrrolidinecarbodithioate
86. 2-Acetylethyl 2-methoxycarbonyl-1-pyrrolidinecarbodithioate
87. 2-Acetylethyl 2-benzyloxycarbonyl-1-pyrrolidinecarbodithioate
88. 2-Acetylethyl 1-piperidinecarbodithioate
89. 2-Acetylethyl 1-hexamethyleneiminecarbodithioate
90. 2-Acetylethyl 3-oxazolidinecarbodithioate
91. 2-Acetylethyl 4-morpholinecarbodithioate
92. 2-Acetylethyl 4-methyl-1-piperazinecarbodithioate
93. 2-Acetylethyl 4-methyl-1-piperazinecarbodithioate hydrochloride
94. Acetonyl dimethyldithiocarbamate
95. Acetonyl diethyldithiocarbamate
96. 3-Phenylacetonyl dimethyldithiocarbamate
97. Cyclohexylcarbonylmethyl dimethyldithiocarbamate
98. 2-Propionylethyl dimethyldithiocarbamate
99. 2-Propionylethyl diethyldithiocarbamate
100. 2-Propionylethyl 1-piperidinecarbodithioate
101. 2-Propionylethyl 4-morphonlinecarbodithioate
102. 2-Propionylethyl 4-methyl-1-piperazinecarbodithioate
103. 2-Propionylethyl 4-methyl-1-piperazinecarbodithioate hydrochloride
104. 2-Isobutyrylethyl dimethyldithiocarbamate
105. 2-Isobutyrylethyl diethyldithiocarbamate
106. 2-Isobutyrylethyl 1-piperidinecarbodithioate
107. 2-Isobutyrylethyl 4-methyl-1-piperazinecarbodithioate
108. 2-Pivaroylethyl dimethyldithiocarbamate
109. 2-Pivaroylethyl diethyldithiocarbamate
110. 2-Pivaroylethyl 1-piperidinecarbodithioate
111. 2-Pivaroylethyl 4-morpholinecarbodithioate
112. 2-Pivaroylethyl 4-methyl-1-piperazinecarbodithioate hydrochloride
113. 2-Heptanoylethyl dimethyldithiocarbamate
114. 2-(4-methylheptanoyl)ethyl dimethyldithiocarbamate
115. 2-Lauroylethyl dimethyldithiocarbamate
116. 2-Lauroylethyl diethyldithiocarbamate
117. 2-(2,2,4,4-Tetramethylvaleryl)ethyl dimethyldithiocarbamate
118. 2-Cyclopentylcarbonylethyl dimethyldithiocarbamate
119. 2-Phenylacetylethyl dimethyldithiocarbamate
120. 2-Phenylacetylethyl diethyldithiocarbamate 121. 2-Phenylacetylethyl 1-piperidinecarbodithioate
122. 2-Phenylacetylethyl 4-methyl-1-piperazinecarbodithioate hydrochloride
123. 2-Hydrocinnamoylethyl dimethyldithiocarbamate
124. 2-(p-Nitrophenylacetyl)ethyl dimethyldithiocarbamate
125. 2-(o-Hydroxyhydrocinnamoyl)ethyl diethyldithiocarbamate
126. 2-(p-Hydroxyhydrocinnamoyl)ethyl diethyldithiocarbamate
127. 2-(m-Methylhydrocinnamoyl)ethyl dimethyldithiocarbamate
128. 2-(p-Methylhydrocinnamoyl)ethyl diethyldithiocarbamate
129. 2-(p-Methoxyhydrocinnamoyl)ethyl diethyldithiocarbamate
130. 2-(o-Chlorohydrocinnamoyl)ethyl dimethyldithiocarbamate
131. 2-(o-Nitrohydrocinnamoyl)ethyl dimethyldithiocarbamate
132. 2-(2-Butenoyl)ethyl dimethyldithiocarbamate
133. 2-(2-Butenoyl)ethyl diethyldithiocarbamate
134. 2-Cinnamoylethyl dimethyldithiocarbamate
135. 2-Cinnamoylethyl diethyldithiocarbamate
136. 2-Cinnamoylethyl 1-piperidinecarbodithioate
137. 2-Cinnamoylethyl 4-methyl-1-piperazinecarbodithioate hydrochloride
138. 2-(2,4-Hexadienoyl)ethyl dimethyldithiocarbamate
139. 2-(o-Hydroxycinnamoyl)ethyl diethyldithiocarbamate
140. 2-(p-Hydroxycinnamoyl)ethyl diethyldithiocarbamate
141. 2-(m-Methylcinnamoyl)ethyl dimethyldithiocarbamate
142. 2-(p-Methylcinnamoyl)ethyl diethyldithiocarbamate
143. 2-(p-Methoxycinnamoyl)ethyl diethyldithiocarbamate
144. 2-(o-Chlorocinnamoyl)ethyl dimethyldithiocarbamate
145. 2-(o-Nitrocinnamoyl)ethyl dimethyldithiocarbamate
146. 2-[β-(2,6,6-Trimethylcyclohexene-1-yl)acryloyl]-ethyl dimethyldithiocarbamate
147. 2-Acetylpropyl dimethyldithiocarbamate
148. 2-Acetylpropyl diethyldithiocarbamate
149. 2-Acetylpropyl 1-piperidinecarbodithioate
150. 2-Acetylpropyl 4-methyl-1-piperazinecarbodithioate hydrochloride
151. 2-Acetylheptyl dimethyldithiocarbamate
152. 2-Acetyldodecyl dimethyldithiocarbamate
153. 2-Acetyldodecyl diethyldithiocarbamate
154. 2-Acetyl-4-methylheptyl dimethyldithiocarbamate
155. 2-Acetyl-2-cyclohexylethyl dimethyldithiocarbamate
156. 2-Acetyl-2-benzylethyl dimethyldithiocarbamate
157. 2-Acetyl-2-benzylethyl diethyldithiocarbamate
158. 2-Acetyl-2-(p-hydroxybenzyl)ethyl dimethyldithiocarbamate
159. 2-Acetyl-2-salicylethyl diethyldithiocarbamate
160. 2-Acetyl-2-(m-methylbenzyl)ethyl dimethyldithiocarbamate
161. 2-Acetyl-2-(p-methylbenzyl)ethyl diethyldithiocarbamate
162. 2-Acetyl-2-(p-anisyl)ethyl diethyldithiocarbamate
163. 2-Acetyl-2-(o-chlorobenzyl)ethyl dimethyldithiocarbamate
164. 2-Acetyl-2-phenylethyl dimethyldithiocarbamate
165. 2-Acetyl-2-phenylethyl diethyldithiocarbamate
166. 2-Acetyl-2-phenylethyl 1-piperidinecarbodithioate
167. 2-Acetyl-2-phenylethyl 4-methyl-1-piperazinecarbodithioate hydrochloride
168. 2-Acetyl-2-(o-tolyl)ethyl dimethyldithiocarbamate
169. 2-Acetyl-2-(m-tolyl)ethyl diethyldithiocarbamate
170. 2-Acetyl-2-(p-tolyl)ethyl dimethyldithiocarbamate
171. 2-Acetyl-2-(p-methoxyphenyl)ethyl dimethyldithiocarbamate
172. 2-Acetyl-2-(o-chlorophenyl)ethyl dimethyldithiocarbamate
173. 2-Acetyl-2-(p-hydroxyphenyl)ethyl dimethyldithiocarbamate
174. 1-Methylacetonyl dimethyldithiocarbamate
175. 1-Methylacetonyl diethyldithiocarbamate
176. 1-Decylacetonyl diethyldithiocarbamate
177. 1-Isopropylacetonyl dimethyldithiocarbamate
178. 1-Cyclohexylacetonyl dimethyldithiocarbamate
179. 1-Benzylacetonyl diethyldithiocarbamate
180. 1-Vinylacetonyl 1-piperidinecarbodithioate
181. 1-Ethynylacetonyl dimethyldithiocarbamate
182. 1-Phenylacetonyl diethyldithiocarbamate
183. 4-Hydroxy-3,5-dimethylbenzyl dimethyldithiocarbamate
184. 4-Hydroxy-3,5-dimethylbenzyl n-butylmethyldithiocarbamate
185. 4-Hydroxy-3,5-dimethylbenzyl cyclohexylmethyldithiocarbamate
186. 4-Hydroxy-3,5-dimethylbenzyl benzylmethyldithiocarbamate
187. 4-Hydroxy-3,5-dimethylbenzyl 1-pyrrolidinecarbodithioate
188. 4-Hydroxy-3,5-dimethylbenzyl 2-carboxy-1-pyrrolidinecarbodithioate
189. 4-Hydroxy-3,5-dimethylbenzyl 2-carboxy-1-pyrrolidinecarbodithioate sodium salt
190. 4-Hydroxy-3,5-dimethylbenzyl 2-methoxycarbonyl-1-pyrrolidinecarbodithioate
191. 4-Hydroxy-3,5-dimethylbenzyl 2-benzyloxycarbonyl-1-pyrrolidinecarbodithioate
192. 4-Hydroxy-3,5-dimethylbenzyl 1-piperidinecarbodithioate
193. 4-Hydroxy-3,5-dimethylbenzyl 3-oxazolidinecarbodithioate
194. 4-Hydroxy-3,5-dimethylbenzyl 4-morpholinecarbodithioate
195. 4-Hydroxy-3,5-dimethylbenzyl 4-methyl-1-piperazinecarbodithioate
196. 4-Hydroxy-3,5-dimethylbenzyl 4-methyl-1-piperazinecarbodithioate hydrochloride
197. 2-Hydroxy-3,5-dimethylbenzyl dimethyldithiocarbamate
198. 2-Hydroxy-3,5-dimethylbenzyl diethyldithiocarbamate
199. 2-Hydroxy-3,5-dimethylbenzyl diethyldithiocarbamate
200. 2-Hydroxy-3,5-dimethylbenzyl 4-methyl-1-piperazinecarbodithioate hydrochloride 201. 4-Hydroxy-2-isopropyl-5-methylbenzyl dimethyldithiocarbamate
202. 4-Hydroxy-2-isopropyl-5-methylbenzyl diethyldithyldithiocarbamate
203. 4-Hydroxy-2-isopropyl-5-methylbenzyl 1-piperidinecarbodithioate
204. 4-Hydroxy-2-isopropyl-5-methylbenzyl 4-morpholinecarbodithioate
205. 4-Hydroxy-2-isopropyl-5-methylbenzyl 4-methyl-1-piperazinecarbodithioate hydrochloride
206. 4-Hydroxy-3-t-butyl-5-methylbenzyl dimethyldithiocarbamate
207. 4-Hydroxy-3-t-butyl-5-methylbenzyl 1-piperidinecarbodithioate
208. 4-Hydroxy-3-t-butyl-5-methylbenzyl 4-methyl-1-piperazinecarbodithioate hydrochloride
209. 4-Hydroxy-3,5-di-isopropylbenzyl dimethyldithiocarbamate
210. 4-Hydroxy-3,5-di-isopropylbenzyl 4-morpholinecarbodithioate
211. 4-Hydroxy-3,5-di-t-butylbenzyl dimethyldithio carbamate
212. 4-Hydroxy-3,5-di-t-butylbenzyl diethyldithiocarbamate
213. 4-Hydroxy-3,5-di-t-butylbenzyl n-butylmethyldithiocarbamate
214. 4-Hydroxy-3,5-di-t-butylbenzyl di-ni-propyldithiocarbamate
215. 4-Hydroxy-3,5di-t-butylbenzyl di-n-butyldithiocarbamate
216. 4-Hydroxy-3,5-di-t-butylbenzyl cyclohexylmethyldithiocarbamate
217. 4-Hydroxy-3,5-di-t-butylbenzly benzylmethyldithiocarbamate
218. 4-Hydroxy-3,5-di-t-butylbenzyl 1-piperidinecarbodithioate
219. 4-Hydroxy-3,5-di-t-butylbenzyl 4-morpholinecarbodithioate
220. 4-Hydroxy-3,5-di-t-butylbenzyl 1-hexamethyleneiminecarbodithioate
221. 4-Hydroxy-3,5-di-t-butylbenzyl 4-methyl-1-piperazinecarbodithioate hydrochloride
222. 4-Hydroxy-3,5-di-t-butyl-α-methylbenzyl dimethyldithiocarbamate
223. 4-Hydroxy-3,5-di-t-butyl-α-cyclohexylbenzyl dimethyldithiocarbamate
224. 4-Hydroxy-3,5-di-t-butyl-α- phenylbenzyl dimethyldithiocarbamate
225. 4-Hydroxy-3,5-di-t-butyl-α-phenylbenzyl 1-piperidinecarbodithioate
226. 4-Hydroxy-3,5-di-t-butyl-α-phenylbenzyl 4-methyl-1-piperazinecarbondithioate hydrochloride
227. 2-Hydroxy-3,5-di-t-butylbenzyl dimethyldithiocarbamate
228. 4-Hydroxy-3,5-dimethoxybenzyl dimethyldithiocarbamate
229. 4-Hydroxy-3,5-dimethoxybenzyl 1-piperidinecarbodithioate
230. 4-Hydroxy-3,5-dimethoxybenzyl 4-morpholinecarbodithioate
231. 4-Hydroxy-3,5-dimethoxybenzyl 4-methyl-1-piperazinecarbodithioate hydrochloride
232. 4-Hydroxy-3,5-dichlorobenzyl dimethyldithiocarbamate
233. 4-Hydroxy-3,5-dichlorobenzyl diethyldithiocarbamate
234. 4-Hydroxy-3,5-dichlorobenzyl 1-piperidinecarbodithioate
235. 4-Hydroxy-3,5-dichlorobenzyl 4-morpholinecarbodithioate
236. 4-Hydroxy-3-dimethylaminomethyl-5-methylbenzyl dimethyldithiocarbamate
237. 4-Hydroxy-3-(methyl-1-piperazinomethyl)-5-methylbenzyl 4-methyl-1-piperazinecarbodithioate dihydrochloride
238. 4-Hydroxy-3-dimethylaminomethyl5-n-propylbenzyl dimethyldithiocarbamate hydrochloride
239. 4-Hydroxy-3-(;b 4-methyl-1-piperazinomethyl)-5-n-propylbenzyl 4-metyl-1-piperazinecarbodithioate dihydrochloride
240. 4-Hydroxy-3-dimethylaminomethyl-5-sec-butylbenzyl dimethyldithiocarbamate hydrochloride
241. 4-Hydroxy-3-dimethylaminomethyl-5-t-butylbenzyl diethyldithiocarbamate
242. 2-Hydroxy-3-methoxy-5-hydroxymethylbenzyl diethyldithiocarbamate
243. 2-Hydroxy-3-methoxy-5-hydroxymetylbenzyl 1-piperidinecarbodithioate
244. 2-Hydroxy-3-methoxy-5-hydroxymethylbenzyl 4-morpholinecarbodithioate
245. 2-Hydroxy-3-methoxy-5-hydroxymethylbenzyl 4-methyl-1-piperazinecarbodithioate hydrochloride
246. 2-Hydroxy-3-methoxy-5-propenylbenzyl diethyldithiocarbamate
247. 4-Hydroxy-5-dimethylthiocarbamoylthiomethyl-2-methylbenzyl dimethyldithiocarbamate
248. 4-Hydroxy-5-dimethylthiocarbamoylthiomethyl-3-n-propylbenzyl dimethyldithiocarbamate
249. 4-Hydroxy-5-(4-methyl-1-piperazinethiocarbonylthiomethyl)-3-n-propylbenzyl 4-methyl-1-piperazinecarbodithioate dihydrochloride
250. 4-Hydroxy-5-dimethylthiocarbamoylthiomethyl-3-sec-butylbenzyl dimethyldithiocarbamate
251. 2-Hydroxy-5-dimethylthiocarbamoylthiomethyl-3-t-butylbenzyl dimethyldithiocarbamate
252. 2-Hydroxy-5-(1-piperidinethiocarbonylthiomethyl)-3-t-butylbenzyl 1-piperidinecarbodithioate
253. 2-Hydroxy-5-(4-methyl-1-piperzonethiocarbonylthiomethyl)-3-t-butylbenzyl 4-methyl-1-piperazinecarbodithioate dihydrochloride
254. 5-Hydroxy-2-hydroxymethyl-4-oxo-4H-pyran-6-ylmethyl dimethyldithiocarbamate
255. 5-Hydroxy-2-hydroxymethyl-4-oxo-4H-pyran-6-ylmethyl diethyldithiocarbamate
256. 5-Hydroxy-2-hydroxymethyl-4-oxo-4H-pyran-6-ylmethyl n-butylmethyldithiocarbamate
257. 5-Hydroxy-2-hydroxymethyl-4-oxo-4H-pyran-6-ylmethyl benzylmethyldithiocarbamate
258. 5-Hydroxy-2-hydroxymethyl-4-oxo-4H-pyran-6-ylmethyl-1-pyrrolidinecarbodithioate
259. 5-Hydroxy-2-hydroxymethyl-4-oxo-4H-pyran-6-ylmethyl-2-methoxycarbonyl-1-pyrrolidinecarbodithioate
260. 5-Hydroxy-2-hydroxymethyl-4-oxo-4H-pyran6-ylmethyl-2-carboxy-1-pyrrolidinecarbodithioate sodium salt
261. 5-Hydroxy-2-hydroxymethyl-4-oxo-4H-pyran-6-ylmethyl-1-piperidinecarbodithioate
262. 5-Hydroxy-2-hydroxymethyl-4-oxo-4H-pyran-6-ylmethyl-4-morpholinecarbodithioate
263. 5-Hydroxy-2-hydroxymethyl-4-oxo-4H-pyran-6-ylmethyl-4-methyl-1-piperazinecarbodithioate
264. 5-Hydroxy-2-hydroxymethyl-4-oxo-4H-pyran-6-ylmethyl-4-methyl-1-piperazinecarbodithioate hydrochloride 265. 16-Dimethylthiocarbamoylthiomethylsiccanin
266. 16-Diethylthiocarbamoylthiomethylsiccanin
267. 16-n-Butylmethylthiocarbamoylthiomethylsiccanin
268. 16-Cyclohexylmethylthiocarbamoylthiomethylsiccanin
269. 16-(1-Pyrrolidinethiocarbonylthiomethyl)siccanin
270. 16-(1-Piperidinethiocarbonylthiomethyl)siccanin
271. 16-(4-Morpholinethiocarbonylthiomethyl)siccanin
272. 16-(4-Methyl-1-piperazinethiocarbonylthiomethyl)-siccanin
273. 16-(4-Methyl-1-piperazinethiocarbonylthiomethyl)siccanin hydrochloride
274. 4-Hydroxy-2,3-dimethyl-5-t-butylbenzyl dimethyldithiocarbamate
275. 4-Hydroxy-2,3-dimethyl-5-t-butylbenzyl diethyldithiocarbamate
276. 4-Hydroxy-2,3-dimethyl-5-t-butylbenzyl 4-morpholinecarbodithioate
277. 4-Hydroxy-2,5-dimethyl-3-dimethylthiocarbamoylthiomethylbenzyl dimethyldithiocarbamate
278. 4-Hydroxy-2,5-dimethyl-3-dimethylaminomethylbenzyl dimethyldithiocarbamate
279. 4-Hydroxy-2,5-dimethyl-3-diethylthiocarbamoylthiomethylbenzyl diethyldithiocarbamate
280. 4-Hydroxy-2,5-dimethyl-3-(4-moropholinothiocarbonylthiomethyl)benzyl 4-morpholinecarbodithioate
281. 4-Hydroxy-5,6-dimethyl-3-dimethylaminomethylbenzyl dimethyldithiocarbamate hydrochloride
282. 4-Hydroxy-5,6-dimethyl-3-diethylthiocarbamoylthiomethylbenzyl diethyldithiocarbamate
283. 4-Hydroxy-5,6-dimethyl-3-(4-methyl-1-piperazinothiocarbonylthiomethyl)benzyl 4-methyl-1-piperazinocarbodithioate dihydrochloride
284. 4-Hydroxy-2,3,5,6-tetramethylbenzyl dimethyldithiocarbamate
285. 4-Hydroxy-2,3,5,6-tetramethylbenzyl diethyldithiocarbamate
286. 4-Hydroxy-2,3,5,6-tetramethylbenzyl 1-piperidinecarbodithioate
287. 4-Hydroxy-2,3,5,6-tetramethylbenzyl 4-methyl-1-piperazinecarbodithioate hydrochloride
288. 4-Hydroxy-2,3,5,6-tetramethylbenzyl 4-morpholinecarbodithioate
289. 4-Chloro-2-dimethylthiocarbamoylthiomethyl-1-naphthol
290. 4-Chloro-2-diethylthiocarbamoylthiomethyl-1-naphthol
291. 4-Chloro-2-(1-piperidinothiocarbonylthiomethyl)-1-naphthol
292. 3-Chloro-2-(4-methyl-1-piperazinothiocarbonylthiomethyl)-1-naphthol hydrochloride
293. 2,4-Bis(dimethylthiocarbamoylthiomethyl-1-naphthol
294. 2,4-Bis(diethylthiocarbamoylthiomethyl)-1-naphthol
295. 2,4-Bis(4-methyl-1-piperazinothiocarbonylthiomethyl)-1-naphthol
296. 1-Dimethylthiocarbamoylthiomethyl-2-naphthol
297. 1-Diethylthiocarbamoylthiomethyl-2-naphthol
298. 1-(4-Methyl-1-piperazinothiocarbonylthiomethyl)-2-naphthol
299. 2-(1-Piperidinothiocarbonylthiomethyl)-1-naphthol
300. 2,4-Bis(4-moropholinothiocarbonylthiomethyl)-1-naphthol
301. 1-(1-Piperidinothiocarbonylthiomethyl)-2-naphthol
302. 1-(4-Morpholinothiocarbonylthiomethyl)-2-naphthol Of the above-listed compounds, there are mentioned the following compounds as a preferable group in view of their activities.

Compound Nos. 1, 2, 3, 5, 6, 7, 9, 12, 23, 24, 30, 31, 34, 42, 55, 56, 57, 61, 69, 78, 79, 80, 81, 82, 88, 89, 91, 92, 93, 99, 101, 104, 108, 123, 125, 129, 134, 135, 142, 146, 147, 148, 149, 152, 156, 164, 176, 178, 183, 187, 192, 197, 198, 199, 202, 207, 210, 211, 218, 219, 225, 229, 232, 236, 238, 240, 241, 242, 246, 248, 250, 251, 254, 255, 265, 266, 272.

The most preferable group of the above-listed compounds are as shown below.

Compound Nos. 1, 2, 3, 5, 6, 7, 9, 12, 23, 24, 30, 31, 34, 42, 55, 56, 57, 69, 78, 79, 80, 81, 82, 88, 89, 91, 92, 93, 99, 101, 104, 108, 123, 125, 129, 134, 135, 142, 147, 148, 149, 152, 156, 164, 176, 178, 183, 202, 207, 219, 232, 236, 238, 242, 248, 250, 251, 255, 266.

Of the above-listed compounds, some of them, manely those having Compound Nos. 21, 22, 23, 24, 33, 34, 78, 94, 95, 174, 175, 183, 192, 194, 197, 207, 211, 212, 218, 219, 225, 227, 229, 236, 238, 240, 241, 248, 250, 251, 274, 277, 278, 284 are known as such, but other derivatives are new substances.

The dithiocarbamic acid derivatives of the present invention represented by the formula (I) can be prepared by either of the following methods.

Process A: A method according to the procedures described in Archiv der pharmazie, 304, 649 (1971).
Starting material

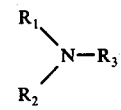

($R_1$, $R_2$ and $R_3$ have the same meanings as above), which is synthesized in a conventional manner by Mannich's reaction, is subjected to reaction with a slight excess of carbon disulfide at a temperature of from room temperature to reflux temperature for 0.5 to 20 hours. After cooling, the desired compound

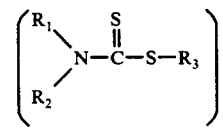

in many cases precipitates. The precipitate is collected by decantation or by filtration and purified by recrystallization from a suitable solvent or by silica gel chromatography. Alternatively, the desired compound may be recovered and purified by removing the solvent, dissolving the residue in benzene and washing the resulting solution successively with a mineral acid and water. The solution is dried over anhydrous sodium sulfate and, if necessary, decolorized with Florisil (trade name of silica gel available from Floridin Co., Ltd,. U.S.A.) and then the solvent is distilled off to give the desired compound (I) as a viscous oil or crystalline substance in a substantially pure state.

In case the starting material is synthesized from an unsymmetric ketone, the material is a mixture of straight-chain and branched isomers. At this time, each of the desired compounds can be obtained from the said mixture by separating each of the isomers and then subjecting each to reaction with carbon disulfide or by treating the mixture as shown below, the treatment being based on the difference of the reaction rate of the isomers with carbon disulfide.

The isomeric mixture (which is previously the approximate ratio of the isomers by thin layer chromatography and nuclear magnetic resonance absorpiton) is dissolved in alcohol. About ⅓-½ of the theoretical amount of carbon disulfide is added thereto and the mixture is subjected to reaction under boiling for about 1-3 hours. The alcohol is removed and the residue is dissolved in benzene, washed with a diluted mineral acid. After washing with water, the benezene layer is dried over anhydrous sodium sulfate and, if necessary, decolorized with Florisil. Thereafter, benzene is removed by evaporation to give a pure straight-chain-type dithiocarbamate. (For example, compound No. 98-107, 113-116, 119-131). The diluted acid washing is made basic and extracted with benzene. After dissolving the extract in alcohol, the theoretical amount of carbon disulfide is added and the mixture is boiled for 3-10 hours. After removing alcohol by evaporation, the residue is dissolved in benzene, and washed with diluted mineral acid and subsequently with water. The benzene layer is dried over anhydrous sodium sulfate and, if necessary, decolorized with Florisil. After removing benzene by evaporation, almost pure branched-type dithiocarbamate (For example, Compound No. 147-173) is obtained.

Process B: A method according to the procedure described in Chem. Ber., 106, 1483 (1973) or in J. Indian Chem. Soc., 51, 440 (1974).

A compound

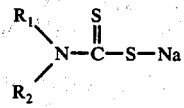

(wherein $R_1$ and $R_2$ have the same meanings as above) and a compound $R_3-X_1$ ($R_3$ is the same as described above and $X_1$ represents a halogen atom) are subjected to reaction at a temperature of from room temperature to boiling temperature for 3-7 hours in a suitable solvent such as dioxane, ethanol, aqueous ethanol, etc. After removing the solvent, the residue is extracted with benzene, washed with water and dried over anhydrous sodium sulfate. The solvent is removed by evaporation to give the desired compound as an almost pure viscous oil or crystalline substance.

According to the above Process A or B, the following compounds were synthesized. In case the compound is a viscous oil, its property is shown by a $R_f$ value. The characterization by chromatography was conducted by using Eastman-chromatogram-sheet-silica gel No 6060 and by developing the chromatogram by 6 cm.

As the developing solvents, ①benzene-ethyl acetate (1:1), ② benzene and ③ n-hexane-benzene (4:1) were used.

The $R_f$ value of each case was shown at ①,② or ③, respectively.

2-Oxocyclopentylmethyl dimethyldithiocarbamate
  mp: 68°-72° C
2-Oxocyclopentylmethyl diethyldithiocarbamate
  viscous oil, $R_f$ ①0.80,②0.45
2-Oxocyclopentylmethyl 4-morpholinecarbodithioate
  mp: 46°-52° C
2-Oxocyclohexylmethyl demethyldithiocarbamate
  viscous oil, $R_f$①0.75,②0.50
2-Oxocyclohexylmethyl diethyldithiocarbamate
  viscous oil, $R_f$ ①0.80②0.55
2-Oxocyclohexylmethyl n-butylmethyldithiocarbamate
  viscous oil, $R_f$①0.90,②0.48
2-Oxocyclohexylmethyl 1-piperidinecarbodithioate
  mp: 32° C
2-Oxocyclohexylmethyl 4-morpholinecarbodithioate
  mp: 94.5°-98° C
2,4,4-Trimethyl-6-oxocyclohexylmethyl 1-piperidinecarbodithioate
  mp: 78°-82° C
2,4,4-Trimethyl-6-oxocyclohexylmethyl 4-morpholinecarbodithioate
  mp: 90°-92° C
3-Isopropyl-6-methyl-2-oxocyclohexylmethyl dimethyldithiocarbamate
  viscous oil, $R_f$①0.78,②0.59
Phenacyl dimethyldithiocarbamate
  mp: 108°-110° C
Phenacyl diethyldithiocarbamate
  mp: 110°-102° C
2-Benzoylethyl dimethyldithiocarbamate
  mp: 45°-47° C
2-Benzoylethyl diethyldithiocarbamate
  mp: 35°-37° C
2-Benzoylethyl n-butylmethyldithiocarbamate
  viscous oil, $R_f$ ①0.85,②0.64
2-Benzoylethyl cyclohexylmethyldithiocarbamate
  viscous oil, $R_f$①0.83,②0.64
2-Benzoylethyl benzylmethyldithiocarbamate
  mp: 58°-61° C
2-Benzoylethyl 1-pyrrolidinecarbodithioate
  mp: 103°-104° C
2-Benzoylethyl 4-morpholinecarbodithioate
  mp: 105°-106° C
2-Benzoylethyl 4-methyl-1-piperazinecarbodithioate
  mp: 86.5°-87.5° C
2-Benzoylethyl 4-methyl-1-piperazinecarbodithioate hydrochloride
  mp: 144°-145° C (decomp.)
2-Benzoylethyl L-2-methoxycarbonyl-1-pyrrolidinecarbodithioate
  viscous oil, $R_f$①0.79,②0.48
2-Benzoylethyl L-2-benzyloxycarbonyl-1-pyrrolidinecarbodithioate
  mp: 57°-58° C
Sodium salt of 2-benzoylethyl L-2-carboxy-1-pyrrolidinecarbodithioate
  mp: 110°-114° C
2-(β-naphthoyl) ethyl dimethyldithiocarbamate
  mp: 94°-96° C
2-(α-naphthoyl)ethyl dimethyldithiocarbamate
  mp: 83°-88° C
2-(o-Hydroxybenzoly)ethyl dimethyldithiocarbamate
  mp: 132°-133° C 2-(o-Hydroxybenzoyl)ethyl 4-morpholinecarbodithioate
mp: 123°–124° C
2-(p-Hydroxybenzoyl)ethyl 4-morpholinecarbodithioate
mp: 155°–157° C
2-(p-Methoxybenzoyl)ethyl 1-pyrrolidinecarbodithioate
mp: 102°–104° C
2-(p-Methoxybenzoyl)ethyl 4-morpholinecarbodithioate
mp: 126°–127° C
2-(p-Chlorobenzoyl)ethyl 4-morpholinecarbodithioate
mp: 124.5;20 –125.5° C
2-(p-Bromobenzoyl)ethyl 4-morpholinecarbodithioate
mp: 122°–123° C
2-(3,4-Dichlorobenzoyl)ethyl dimethyldithiocarbamate
mp: 104°–106° C
2-(3,4-Dichlorobenzoyl)ethyl 4-moropholinecarbodithioate
mp: 131.5°–132.5° C
2-(p-Toluoyl)ethyl dimethyldithiocarbamate
mp: 104°–106° C
2-(m-Toluoyl)ethyl dimethyldithiocarbamate
mp: 41°–43° C
2-(o-Toluoyl)ethyl dimethyldithiocarbamate
mp: 58°–62° C
2-(o-Nitrobenzoyl)ethyl 4-morpholinecarbodithioate
mp: 101°–102° C
2-(m-Nitrobenzoyl)ethyl 4-morpholinecarbodithioate
mp: 106°–108° C
2- (p-Nitrobenzoyl)ethyl 4-morpholinecarbodithioate
mp: 135°–136° C
2-(2-Furoyl)ethyl 4-morpholinecarbodithioate
mp: 127°–128° C
2-(2-Thenoyl)ethyl 4-morpholinecarbodithioate
mp: 106°–107° C
2-Nicotinoylethyl dimethyldithiocarbamate
mp: 88°–89° C
2-Acetylethyl dimethyldithiocarbamate
viscous oil, $R_f$ ①0.78 ②0.43
2-Acetylethyl diethyldithiocarbamate
viscous oil, $R_f$ ①0.83 ②0.63
2-Acetylethyl butylmethyldithiocarbamate
viscous oil, $R_f$ ①0.83 ②0.63
2-Acetylethyl cyclohexylmethyldithiocarbamate
viscous oil, $R_f$ ①0.88 ②0.62
2-Acetylethyl benzylmethyldithiocarbamate
viscous oil, $R_f$ ①0.83 ②0.58
2-Acetylethyl 2-carboxy-1-pyrrolidinecarbodithioate
mp: 118°–120° C
sodium salt of 2-acetylethyl 2-carboxy-1-pyrrolidinecarbodithioate
mp: 80°–130°C (decomp.)
2-Acetylethyl 2-benzyloxycarbonyl-1-pyrolidinecarbodithioate
viscous oil, $R_f$ ①0.83 ②0.32
2-Acetylethyl 1-piperidinecarbodithioate
viscous oil, $R_f$ ①0.78 ②0.47
2-Acetylethyl 1-hexamethyleneiminecarbodithioate
viscous oil, $R_f$ ①0.83 ②0.59
2-Acetylethyl 4-morpholinecarbodithioate
viscous oil, $R_f$ ①0.75 ②0.26
2-Acetylethyl 1-methyl-4-piperazinecarbodithioate
viscous oil, $R_f$ ①0.37 ②0.08
2-Acetylethyl 1-methyl-4-piperazinecarbodithioate hydrochloride
mp: 130°–132° C
Acetonyl dimethyldithiocarbamate
mp: 55°–56° C
Acetonyl diethyldithiocarbamate
viscous oil, $R_f$ ①0.70 ②0.57
2-Propionylethyl diethyldithiocarbamate
viscous oil, $R_f$ ①0.84 ②0.63
2-Propionylethyl 4-morpholinecarbodithioate
viscous oil, $R_f$ ①0.87 ②0.30
2-Isobutyrylethyl dimethyldithiocarbamate
viscous oil, $R_f$ ①0.87 ②0.60
2-Pivaroylethyl dimethyldithiocarbamate
viscous oil, $R_f$ ①0.83 ②0.63
2-Lauroylethyl dimethyldithiocarbamate
mp: 47°–48° C
2-Hydrocinnamoylethyl dimethyldithiocarbamate
viscous oil, $R_f$ ①0.83 ②0.57
2-(p-Methoxyhydrocinnamoyl)ethyl diethyldithiocarbamate
viscous oil $R_f$ ①0.83 ②0.52
2-Cinnamoylethyl dimethyldithiocarbamate
viscous oil, $R_f$ ①0.80 ②0.58
2-(p-Methoxycinnamoyl)ethyl diethyldithiocarbamate
mp: 76°–79° C
2-[β-(2,6,6-Trimethylcyclohexene-1-yl)acryloyl]ethyl dimethyldithiocarbamate
viscous oil, $R_f$ ①0.90 ②0.49
2-Acetylpropyl dimethyldithiocarbamate
viscous oil, $R_f$ ①0.79 ②0.40
2-Acetylpropyl diethyldithiocarbamate
viscous oil, $R_f$ ①0.87 ②0.59
2-Acetylpropyl 1-piperidinecarbodithioate
viscous oil, $R_f$ ①0.81 ②0.41
2-Acetyldodecyl dimethyldithiocarbamate
viscous oil, $R_f$ ①0.87 ②0.64
2-Acetyl-2-benzylethyl dimethyldithiocarbamate
viscous oil, $R_f$ ①0.79 ②0.58
2-Acetyl-2-(p-anisyl)ethyl diethyldithiocarbamate
viscous oil, $R_f$ ①0.81 ②0.48
2-Acetyl-2-phenylethyl dimethyldithiocarbamate
mp: 88°–89° C
1-Methylacetonyl dimethyldithiocarbamate
viscous oil, $R_f$ ①0.80 ②0.58
1-Methylacetonyl diethyldithiocarbamate
viscous oil, $R_f$ ①0.84 ②0.67
2-Cinnamoylethyl diethyldithiocarbamate
mp: 40°–45° C
2-(o-Hydroxyhydrocinnamoyl)ethyl diethyldithiocarbamate
viscous oil, $R_f$ ①0.81 ②0.35
2-(p-Methylhydrocinnamoyl)ethyl diethyldithiocarbamate
viscous oil, $R_f$ ①0.86 ②0.66
2-(o-Hydroxycinnamoyl)ethyl diethyldithiocarbamate
mp: 120°–121° C
2-(p-Methylcinnoamoyl)ethyl diethyldithiocarbamate
viscous oil, $R_f$ ①0.81 ②0.58
2-Acetyl-2-salicylethyl diethyldithiocarbamate
viscous oil, $R_f$ ①0.81 ②0.23
2Acetyl-2-(p-methylbenzyl)ethyl diethyldithiocarbamate
viscous oil, $R_f$ ①0.89 ②0.67
1-Phenylacetonyl diethyldithiocarbamate viscous oil, R_f ①0.82 ②0.57
4-Hydroxy-3,5-dimethylbenzyl dimethyldithiocarbamate
mp: 93°–94° C
4-Hydroxy-3,5-dimethylbenzyl 1-pyrrolidinecarbodithioate
mp: 153°–155° C
4-Hydroxy-3,5-dimethylbenzyl 2-benzyloxycarbonyl-1-pyrrolidinecarbodithioate
viscous oil, R_f ①0.77 ②0.38
4-Hydroxy-3,5-dimethylbenzyl 1-piperidinecarbodithioate
mp: 108°–109° C
4-Hydroxy-3,5-dimethylbenzyl 4-morpholinecarbodithioate
mp: 125°–127° C
4-Hydroxy-3,5-dimethylbenzyl 4-methyl-1-piperazinecarbodithioate hydrochloride
mp: 174°–176° C (decomp.)
2-Hydroxy-3,5-dimethylbenzyl dimethyldithiocarbamate
mp: 121°–123° C
2-Hydroxy-3,5-dimethylbenzyl diethyldithiocarbamate
mp: 79°–81° C
2-Hydroxy-3,5-dimethylbenzyl 1-piperidinocarbodithioate
mp: 115°–118° C
4-Hydroxy-2-isopropyl-5-methylbenzyl diethyldithiocarbamate
mp: 71°–73° C
4-Hydroxy-2-isopropyl-5-methylbenzyl 4-morpholinecarbodithioate
mp: 139°–141° C
4-Hydroxy-3-t-butyl-5-methylbenzyl 1-piperidinecarbodithioate
mp: 103°–105° C
4-Hydroxy-3,5-di-isopropylbenzyl 4-morpholinecarbodithioate
mp: 116.5°–118.5° C
4-Hydroxy-3,5-di-t-butylbenzyl dimethyldithiocarbamate
mp: 139°–141° C
4-Hydroxy-3,5-di-t-butylbenzyl diethyldithiocarbamate
viscous oil, R_f ②0.83
4-Hydroxy-3,5-di-t-butylbenzyl n-butylmethyldithiocarbamate
viscous oil, R_f ③0.23
4-Hydroxy-3,5-di-t-butylbenzyl di-n-propyldithiocarbamate
viscous oil, R_f ③0.40
4-Hydroxy-3,5-di-t-butylbenzyl di-n-butyldithiocarbamate
viscous oil, R_f ③0.47
4-Hydroxy-3,5-di-t-butylbenzyl cyclohexylmethyldithiocarbamate
viscous oil, R_f ③0.30
4-Hydroxy-3,5-di-t-butylbenzyl benzylmethyldithiocarbamate
mp: 103°–107° C
4-Hydroxy-3,5-di-t-butylbenzyl 1-piperidinecarbodithioate
mp: 109.5°–110.5° C
4-Hydroxy-3,5-di-t-butylbenzyl 4-morpholinecarbodithioate
mp: 114°–115° C
4-Hydroxy-3,5-di-t-butylbenzyl 1-hexamethyleneiminecarbodithioate
viscous oil, R_f ①0.89 ②0.83
4-Hydroxy-3,5-di-t-butyl-α-phenylbenzyl 1-piperidinecarbodithioate
mp: 112°–114° C
2-Hydroxy-3,5-di-t-butylbenzyl dimethyldithiocarbamate
mp: 193°–195° C
4-Hydroxy-3,5-dimethoxybenzyl 1-piperidinecarbodithioate
mp: 99°–98° C
4-Hydroxy-3,5-dimethoxybenzyl 4-morpholinecarbodithioate
mp: 132°–134° C
4-Hydroxy-3,5-dichlorobenzyl dimethyldithiocarbamate
mp: 134°–136° C
4-Hydroxy-3,5-dichlorobenzyl 1-piperidinecarbodithioate
mp: 177°–178° C (decomp.)
4-Hydroxy-3,5-dichlorobenzyl 4-morpholinecarbodithioate
mp: 156°–157° C
4-Hydroxy-3-dimethylaminomethyl-5-methylbenzyl dimethyldithiocarbamate
mp: 98°–101° C
4-Hydroxy-3-dimethylaminomethyl-5-n-propylbenzyl dimethyldithiocarbamate hydrochloride
mp: 133°–135° C
4-Hydroxy-3-dimethylaminomethyl-5-sec-butylbenzyl dimethyldithiocarbamate hydrochloride
mp: 148°–149° C
4-Hydroxy-3-dimethylaminomethyl-5-t-butylbenzyl dimethyldithiocarbamate hydrochloride
mp: 223°–224° C
2-Hydroxy-3-methoxy-5-hydroxymethylbenzyl diethyldithiocarbamate
mp: 108°–110° C
2-Hydroxy-3-methoxy-5-hydroxymethylbenzyl 4-morpholinecarbodithioate
mp: 140°–142° C
2-Hydroxy-3-methoxy-5-propenylbenzyl diethyldithiocarbamate
mp: 98.5°–100.5° C
4-Hydroxy-5-dimethylthiocarbamoylthiomethyl-2-methylbenzyl dimethyldithiocarbamate
mp: 140°–143° C
4-Hydroxy-5-dimethylthiocarbamoylthiomethyl-3-n-propylbenzyl dimethyldithiocarbamate
mp: 97°–98° C
4-Hydroxy-5-dimethylthiocarbamoylthiomethyl-3-sec-butylbenzyl dimethyldithiocarbamate
mp: 140°–142° C
2-Hydroxy-5-dimethylthiocarbamoylthiomethyl-3-t-butylbenzyl dimethyldithiocarbamate
mp: 135°–137° C
5-Hydroxy-2-hydroxymethyl-4-oxo-4H-pyran-6-ylmethyl dimethyldithiocarbamate
mp: 148°–149° C (decomp.)
5-Hydroxy-2-hydroxymethyl-4-oxo-4H-pyran-6-ylmethyl diethyldithiocarbamate
mp: 109°–111° C (decomp.)
5-Hydroxy-2-hydroxymethyl-4-oxo-4H-pyran-6-ylmethyl 1-pyrrolidinecarbodithioate
mp: 167.5°–168.5° C (decomp.)
5-Hydroxy-2-hydroxymethyl-4-oxo-4H-pyran-6-yimethyl-1-piperidinecarbodithioate mp: 158°–158.5° C (decomp.)
5-Hydroxy-2-hydroxymethyl-4-oxo-4H-pyran-6-ylmethyl-4-morpholinecarbodithioate
mp: 141°–142° C (decomp.)
5-Hydroxy-2-hydroxymethyl-4-oxo-4H-pyran-6-ylmethyl-4-methyl-1-piperazinecarbodithioate
mp: 166°–167° C (decomp.)
16-Dimethylthiocarbamoylthiomethylsiccanin
mp: 216°–218° C (decomp.)
16-Diethylthiocarbamoylthiomethylsiccanin
mp: 202°–203° C (decomp.)
16-(1-Pyrrolidinethiocarbonylthiomethyl)siccanin
mp: 227°–229° C
16-(4-Morpholinethiocarbonylthiomethyl)siccanin
mp: 178°–179°
16-(4-Methyl-1-piperazinethiocarbonylthiomethyl)-siccanin
mp: 155°–156° C
16-(4-Methyl-1-piperazinethiocarbonylthiomethyl)-siccanin hydrochloride
mp: 150°–160° C
4-Hydroxy-2,5-dimethyl-3-dimethylthiocarbamoyl-thiomethylbenzyl dimethyldithiocarbamate
mp: 163°–165° C
4-Hydroxy-2,5-dimethyl-3-dimethylaminomethyl-benzyl dimethyldithiocarbamate
mp: 143°–145° C
4-Hydroxy-5,6-dimethyl-3-dimethylaminomethyl-benzyl dimethyldithiocarbamate hydrochloride
mp: 139°–141° C
4-Hydroxy-2,3,5,6-tetramethylbenzyl dimethyldithiocarbamate
mp: 177°–178° C
4-Chloro-2-(1-piperidinothiocarbonylthiomethyl)-1-naphthol
mp: 115°–116° C
2-(1-Piperidinothiocarbonylthiomethyl)-1-naphthol
viscous oil, $R_f$ ② 0.67
2,4-Bis(4-morpholinothiocarbonylthiomethyl)-1-naphthol
mp: 158°–159° C
1-(1-Piperidinothiocarbonylthiomethyl)-2-naphthol
mp: 130°–134° C
1-(4-Morpholinothiocarbonylthiomethyl)-2-naphthol
mp: 123°–124° C According to one aspect of this invention, there is provided a preventive and curative composition against mycoplasmosis which comprises as an active ingredient the dithiocarbamic acid derivative (I) and an inert carrier. The term "inert carrier" as used herein means one that is substantially non-reactive with the active ingredient, orally ingestable and tolerated by the poultry and domestic animals. Representative examples of the carriers to be employed in this invention are solid oral carriers such as distillers dried grains, corn starch, potato starch, fermentation residues, ground oyster shells, Attapulgus clay, rice bran, wheat bran, wheat middling, molasses solubles, corn husks, corn meal, edible vegetable substances, soybean cake, soybean meal, antibiotic mycelis, crushed lime stone and the like.

The amount of dithiocarbamic acid derivative required for control of mycoplasmosis in poultry will vary somewhat with the specific compound employed, the species of animals, the method or the object of application or with the symptoms. Generally, the dithiocarbamic acid derivatives (I) are effective in preventing the disease without undesirable side effect and toxic effect when administered at a level of more than about 0.005% by weight of the feed. For good prophylactic results, it is preferred that the feed contains between about 0.005 and 0.02% by weight of the active ingredient, more preferably between about 0.0075 and 0.01%. When the dithiocarbamic acid derivatives are to be employed for therapeutic purpose, the higher levels are used for a shorter period of time. Thus, the concentrations of about 0.01 to about 0.1% by weight, preferably 0.02 to 0.05% by weight, of the feed may be advantageously administered for treatment of mycoplasmosis. When these compounds are to be employed for therapeutic purpose, it is desirable to employ the lowest levels that exhibit anti-mycoplasmosis activities, in order to eliminate any risk of side effects that may appear on prolonged feeding.

In preparing solid compositions, a uniform dispersion of the active ingredient throughout the carrier can be readily accomplished by the conventional methods of grinding, stirring or milling.

Many of these dithiocarbamic acid derivatives are advantageously administered to poultry by way of the drinking water of the birds. This method of treatment may often be employed in the therapeutic use, since poultry with mycoplasmosis are apt to consume less solid feed than normal birds.

According to still another aspect of this invention, novel compositions are provided in which active ingredient is present in relatively large amounts and which are suitable for addition to the poultry feed directly or after intermediate dilution step. Such compositions which are a preferred feature of this invention are the so-called feed supplements or premix.

Formulations containing from about 5% to about 30% by weight, and preferably from about 10–25% by weight, of the active ingredient are particularly suitable for this purpose. It is preferable in the industry to use about 1–3 kg. of such a supplement per ton of feed.

The present composition as prepared above may include other preventive and curative agents against mycoplasmosis, for example, chlorotetracycline, streptomycin, spiramycin, erythromycin, taylocin, etc., or more than one compound of the above formula (I). When two compounds of the formula (I) are synthesized as a mixture, for example, a mixture of a straight-chain and branched isomers, it is unnecessary to separate the isomers and the mixture itself can be added to a feed as a preventive and curative agent.

The concentration to be administered of the preventive and curative agent against mycoplasmosis in the present invention may vary upon the species of poultry or domestic animals, the method or purpose of administration, the severity of the symptom, etc., but 20–400 ppm may be used for preventive and curative purposes in admixture with a feed.

Some examples of the formulation for feed supplements according to this invention are shown below. In these examples, all parts are given by weight unless otherwise indicated.

| Formulation A | Parts |
| --- | --- |
| Compound No. 12 | 25 |
| wheat bran | 75 |
| Formulation B | Parts |
| Compound No. 92 | 20 |
| rice bran | 80 |
| Formulation C | Parts |
| Compound No. 202 | 10 |
| wheat bran | 60 |

| -continued | |
|---|---|
| soybean meal | 30 |

In order to demonstrate the excellent antimicrobial activity against mycoplasmosis of the dithiocarbamic acid derivatives (I) in this invention, there are given below the two Experiments and the results therefrom.

EXPERIMENT 1

ANTIMICROBIAL TEST AGAINST THREE STRAINS OF MYCOPLASMA

The test was effected by a conventional agar plate dilution method using the indicated strains of mycoplasma. The dithiocarbamic acid derivatives as shown below with Compound Nos. were employed in the test. The results are summarized in Table 1.

Table 1

| Test compound(No.) | Minimum Inhibitory Concentration (mcg/ml) | | |
|---|---|---|---|
| | *Mycoplasma gallisepticum* | *Mycoplasma pulmonis* | *Mycoplasma hyorhinis* |
| 1 | 0.05 | 0.05 | 0.05 |
| 2 | 0.10 | 0.10 | 0.10 |
| 3 | 0.20 | 0.10 | 0.20 |
| 5 | 0.05 | 0.10 | 0.05 |
| 6 | 0.10 | 0.10 | 0.05 |
| 7 | 0.20 | 0.20 | 0.20 |
| 9 | 0.20 | 0.39 | 0.20 |
| 12 | 0.05 | 0.20 | 0.39 |
| 23 | 0.05 | 0.025 | 0.05 |
| 24 | 0.05 | 0.20 | 0.39 |
| 30 | 0.20 | 0.20 | 0.20 |
| 31 | 0.20 | 0.20 | 0.20 |
| 34 | 0.05 | 0.05 | 0.05 |
| 42 | 0.20 | 0.20 | 0.39 |
| 55 | 0.20 | 0.39 | 0.20 |
| 56 | 0.10 | 0.10 | 0.05 |
| 57 | 0.10 | 0.20 | 0.10 |
| 61 | 0.10 | 0.39 | 1.56 |
| 69 | 0.10 | 0.10 | 0.10 |
| 78 | 0.05 | 0.05 | 0.025 |
| 79 | 0.012 | 0.012 | 0.012 |
| 80 | 0.10 | 0.10 | 0.10 |
| 81 | 0.20 | 0.20 | 0.20 |
| 82 | 0.20 | 0.20 | 0.20 |
| 88 | 0.05 | 0.05 | 0.025 |
| 89 | 0.20 | 0.10 | 0.10 |
| 91 | 0.20 | 0.20 | 0.025 |
| 92 | 0.20 | 0.20 | 0.025 |
| 93 | 0.10 | 0.10 | 0.05 |
| 99 | 0.05 | 0.05 | 0.05 |
| 101 | 0.10 | 0.10 | 0.10 |
| 104 | 0.20 | 0.20 | 0.20 |
| 108 | 0.20 | 0.20 | 0.20 |
| 123 | 0.20 | 0.20 | 0.20 |
| 125 | 0.20 | 0.20 | 0.20 |
| 129 | 0.20 | 0.20 | 0.20 |
| 134 | 0.20 | 0.20 | 0.20 |
| 135 | 0.20 | 0.20 | 0.20 |
| 142 | 0.20 | 0.20 | 0.20 |
| 146 | 0.39 | 0.39 | 0.39 |
| 147 | 0.05 | 0.05 | 0.05 |
| 148 | 0.05 | 0.05 | 0.05 |
| 149 | 0.20 | 0.20 | 0.05 |
| 152 | 0.10 | 0.10 | 0.39 |
| 156 | 0.20 | 0.20 | 0.20 |
| 164 | 0.10 | 0.10 | 0.10 |
| 183 | 0.20 | 0.20 | 0.20 |
| 187 | 0.78 | 0.78 | 0.78 |
| 191 | 1.56 | 1.56 | 3.13 |
| 192 | 0.39 | 0.39 | 0.10 |
| 194 | 1.56 | 1.56 | 0.78 |
| 196 | 1.56 | 1.56 | 0.39 |
| 197 | 0.39 | 0.39 | 0.20 |
| 198 | 0.39 | 0.39 | 0.20 |
| 199 | 0.39 | 0.39 | 0.39 |
| 202 | 0.10 | 0.10 | 0.10 |
| 207 | 0.10 | 0.10 | 0.10 |
| 210 | 0.39 | 0.39 | 0.39 |
| 211 | 0.78 | 0.78 | 0.39 |
| 212 | 1.56 | 1.56 | 1.56 |
| 218 | 0.78 | 0.39 | 0.39 |
| 219 | 0.20 | 0.20 | 0.10 |
| 220 | 0.78 | 0.78 | 0.78 |
| 225 | 0.39 | 0.20 | 0.39 |
| 229 | 0.39 | 0.39 | 0.39 |
| 230 | 1.56 | 1.56 | 0.78 |
| 232 | 0.39 | 0.39 | 0.20 |
| 234 | 3.13 | 3.13 | 1.56 |
| 235 | 1.56 | 1.56 | 1.56 |
| 236 | 0.20 | 0.20 | 0.20 |
| 238 | 0.20 | 0.20 | 0.20 |
| 240 | 0.39 | 0.39 | 0.20 |
| 241 | 0.78 | 0.39 | 0.39 |
| 242 | 0.10 | 0.10 | 0.10 |
| 246 | 0.39 | 0.20 | 0.39 |
| 247 | 0.78 | 0.78 | 0.39 |

Table 1-continued

| Test compound(No.) | Species submitted to the test | Minimum Inhibitory Concentration (mcg/ml) | | |
|---|---|---|---|---|
| | | Mycoplasma gallisepticum | Mycoplasma pulmonis | Mycoplasma hyorhinis |
| 248 | | 0.10 | 0.10 | 0.20 |
| 250 | | 0.20 | 0.20 | 0.20 |
| 251 | | 0.20 | 0.10 | 0.20 |
| 254 | | 0.39 | 0.39 | 0.39 |
| 255 | | 0.05 | 0.10 | 0.05 |
| 258 | | 0.78 | 0.78 | 0.39 |
| 261 | | 3.13 | 3.13 | 3.13 |
| 262 | | 0.20 | 0.78 | 0.78 |
| 263 | | 1.56 | 3.13 | 3.13 |
| 265 | | 0.39 | 0.39 | 0.39 |
| 266 | | 0.10 | 0.10 | 0.10 |
| 271 | | 1.56 | 1.56 | 1.56 |
| 272 | | 0.39 | 0.39 | 0.39 |
| 273 | | 0.78 | 0.78 | 0.78 |

Though the sensitivity of the species to these compounds varies slightly depending upon the kind of the species, all of these compounds have a strong antimicrobial activity against *mycoplasma gallisepticum* which has been considered to cause the chronic respiratory disorders of chicken in particular.

EXPERIMENT 2

Each of the dithiocarbamic acid derivatives as indicated below with Compound No. was added to a feed and administered orally to mice infected artificially with MRL-4 strain of *mycoplasma pulmonis*. The effectiveness of the treatment was evaluated. Six groups, each group consisting of ten female mice which were negative in the test for mycoplasmosis, were used. After MRL-4 strain of *mycoplasma pulmonis* was cultured in PPLO agar medium, the colonies of the surface of the medium were diluted with a phosphate buffer solution to prepare a solution containing about $10^9$/ml of mycoplasma. 0.1 ml of the microbe-containing solution was injected intravenously to the tail of each mouse. For consecutive 10 days from the next day of the injection, the mice were fed with a powdery feed containing the active compound at respective concentrations of 0.04, 0.02, 0.01 and 0.005%, respectively. During the experiment period, all the procedures were conducted in a vinyl isolater.

After one month from the starting of the experiment, the presence of arthritis was visually investigated and at the same time the presence of pneumonia was also investigated after dissection. Recovery tests of mycoplasma and general bacteria were conducted using the joints and lungs of host subjects as the testing materials.

The results are summarized in Table 2.

Table 2

Curative effect of dithiocarbamic acid derivatives in mice by oral administration in feed

| (i) Compound No. | 12 | | | | 24 | | | |
|---|---|---|---|---|---|---|---|---|
| Concentration of agent | Attack rate | | Recovery of mycoplasma | | Attack rate | | Recovery of mycoplasma | |
| | arthritis | pneumonia | joint | lung | arthritis | pneumonia | joint | lung |
| 0.04% | 0/10 | 0/10 | 0/10 | 0/10 | 0/10 | 0/10 | 0/10 | 0/10 |
| 0.02 | 1/10 | 0/10 | 1/10 | 0/10 | 2/10 | 0/10 | 2/10 | 0/10 |
| 0.01 | 4/10 | 0/10 | 4/10 | 0/10 | 3/10 | 0/10 | 3/10 | 0/10 |
| 0.005 | 6/10 | 0/10 | 6/10 | 0/10 | 4/10 | 0/10 | 4/10 | 0/10 |
| Non-infected control | 0/10 | 0/10 | 0/10 | 0/10 | 0/10 | 0/10 | 0/10 | 0/10 |
| Infected control | 10/10 | 0/10 | 10/10 | 0/10 | 10/10 | 0/10 | 10/10 | 0/10 |

| (ii) Compound No. | 88 | | | | 79 | | | |
|---|---|---|---|---|---|---|---|---|
| Concentration of agent | Attack rate | | Recovery of mycoplasma | | Attack rate | | Recovery of mycoplasma | |
| | arthritis | pneumonia | joint | lung | arthritis | pneumonia | joint | lung |
| 0.04% | 0/10 | 0/10 | 0/10 | 0/10 | 0/10 | 0/10 | 0/10 | 0/10 |
| 0.02 | 0/10 | 0/10 | 0/10 | 0/10 | 0/10 | 0/10 | 0/10 | 0/10 |
| 0.01 | 1/10 | 0/10 | 1/10 | 0/10 | 0/10 | 0/10 | 0/10 | 0/10 |
| 0.005 | 3/10 | 0/10 | 3/10 | 0/10 | 2/10 | 0/10 | 2/10 | 0/10 |
| non-infected control | 0/10 | 0/10 | 0/10 | 0/10 | 0/10 | 0/10 | 0/10 | 0/10 |
| infected control | 10/10 | 0/10 | 10/10 | 0/10 | 10/10 | 0/10 | 10/10 | 0/10 |

As shown in Table 2, the appearance of arthritis on the mice to which the active compounds in this invention was administered is sufficiently low in comparison with that of the control groups. Microbe was entirely negative except in the joint affected by arthritis. In all of the infected non-medicated control, arthritis was observed. But, in the group to which 0.04% of each of the present compounds, arthritis was not detected. Even in the group to which 0.005% of the compounds, 70-80% was effectively treated with the present compounds.

What is claimed is:

1. A preventive and curative composition against mycoplasmosis which comprises an effective amount of an active ingredient a compound having the formula

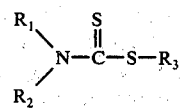

wherein
R₁ and R₂ form, jointly with the nitrogen atom to which they are attached, a 6-membered heteroalicyclic ring which also contains oxygen as another hetero atom and which may be substituted with alkyl of 1 to 4 carbon atoms; and
R₃ is a group —CH₂—R₄ in which R₄ is a 5–7 membered 2-oxocycloalkyl group optionally substituted with 1–3 $C_1$–$C_4$ alkyl groups;
a group

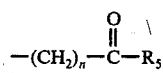

in which n is an integer of 1 or 2 and R₅ is naphthyl group, a phenyl group optionally substituted with 1–2 groups selected from the group consisting of hydroxy, $C_1$–$C_{12}$ alkyl, $C_1$–$C_4$ alkoxy, nitro and halogen or a 5–7 membered heterocyclic group which has as hetero atom 1 or 2 atoms of oxygen atom, nitrogen atom and sulfur atoms and may be substituted with 1–3 groups selected from the group consisting of $C_1$–$C_4$ alkyl, hydroxy, hydroxymethyl, halogenomethyl, dihalogenomethyl, trihalogenomethyl, nitro and halogen;
a group

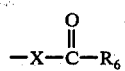

in which R₆ is an alkyl group of 1 to 12 carbon atoms, a 5–6 membered cycloalkyl group, an aralkyl group which has 6 or 10 carbon atoms in the aryl moiety and 1 to 4 carbon atoms in the alkyl moiety and may be substituted with $C_1$–$C_4$ alkyl, hydroxy, nitro, $C_1$–$C_4$ alkoxy or halogen or an alkenyl group of 2 to 5 carbon atoms which may be substituted with cycloalkenyl or phenyl, said phenyl being optionally substituted with $C_1$–$C_4$ alkyl, hydroxy, nitro, $C_1$–$C_4$ alkoxy or halogen and X is a group

wherein R₇ is hydrogen, $C_1$–$C_{12}$ alkyl, cyclohexyl, aralkyl of C₆ or C₁₀ in the aryl moiety and $C_1$–$C_4$ in the alkyl moiety, $C_2$–$C_4$ alkenyl, $C_2$–$C_3$ alkynyl or phenyl or a group

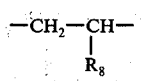

wherein R₈ is hydrogen, $C_1$–$C_{12}$ alkyl, cyclohexyl, aralkyl of C₆ or C₁₀ in the aryl moiety and $C_1$–$C_4$ in the alkyl moiety, said aryl moiety being optionally substituted with $C_1$–$C_4$ alkyl, hydroxy, $C_1$–$C_4$ alkoxy or halogen, or phenyl optionally substituted with $C_1$–$C_4$ alkyl, hydroxy, $C_1$–$C_4$ alkoxy or halogen; or
a group

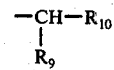

in which R₉ is hydrogen atom, an alkyl group of 1 to 4 carbon atoms, cyclohexyl group or phenyl group and R₁₀ is a phenyl group which has one hydroxy group at the o- or p-position and 2–4 groups selected from the group consisting of $C_1$–$C_4$ alkyl, halogen, $C_1$–$C_4$ alkoxy, $C_2$–$C_4$ alkenyl, hydroxyalkyl of $C_1$–$C_4$, a group

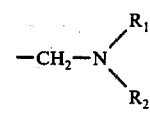

wherein R₁ and R₂ are as defined above and a group

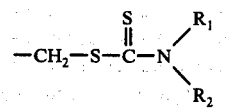

wherein R₁ and R₂ are as defined above, a naphthyl group which has one hydroxy group at the 1- or 2-position and optionally halogen or a group

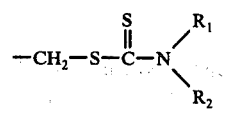

wherein R₁ and R₂ are as defined above, a group

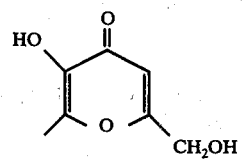

or a group

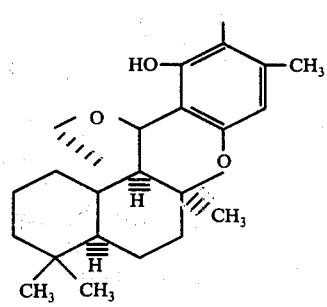

or a salt thereof and an inert carrier.
2. A composition according to claim 1 wherein R₁ and R₂ form, jointly with the nitrogen atom to which they are attached, a 6-membered heteroalicyclic ring which also contains oxygen as another hetero atom and which may be substituted with alkyl of 1 to 4 carbon atoms; and $R_4$ is a 5-6 membered 2-oxocycloalkyl group optionally substituted with 1-2 $C_1$-$C_4$ alkyl groups;

n is 2 and $R_5$ is naphthyl group, a phenyl group optionally substituted with 1-2 groups selected from the group consisting of hydroxy, $C_1$-$C_8$ alkyl, nitro and halogen or a 5-6 membered heterocyclic group which has as hetero atom 1 or 2 atoms of oxygen atom and nitrogen atom;

$R_6$ is an alkyl group of 1 to 12 carbon atoms, a phenethyl group which may be substituted with methyl, hydroxy, methoxy or halogen, an alkenyl group of 3 carbon atoms or a styryl group which may be substituted with methyl hydroxy, methoxy or halogen and X is a group

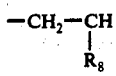

wherein $R_8$ is hydrogen, $C_1$-$C_{12}$ alkyl, cyclohexyl, benzyl optionally substituted with methyl, hydroxy or methoxy or phenyl; or $R_9$ is hydrogen atom, methyl group cyclohexyl group or phenyl group and $R_{10}$ is a phenyl group which has one hydroxy group at the o- or p-position and 2-4 groups selected from the group consisting of $C_1$-$C_4$ alkyl, chlorine, methoxy, propenyl, hydroxymethyl, a group

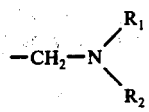

wherein $R_1$ and $R_2$ are as defined above and a group

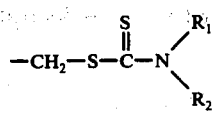

wherein $R_1$ and $R_2$ are as defined above, naphthyl group, a group

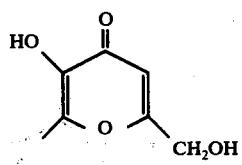

or a group

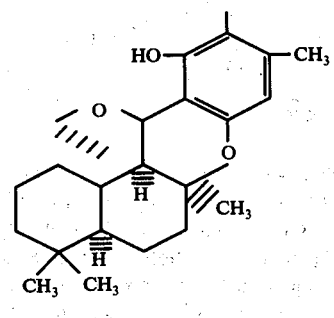

3. A composition according to claim 1 wherein $R_1$ and $R_2$ form; jointly with the nitrogen atom to which they are attached, a 6-membered heteroalicyclic ring which also contains oxygen as another hetero atom and which may be substituted with methyl; and $R_4$ is a 5-6 membered 2-oxoxcycloalkyl group;

n is 2 and $R_5$ is naphthyl group, a phenyl group optionally substituted with 1-2 groups selected from the group consisting of hydroxy, $C_1$-$C_8$ alkyl, nitro and chlorine or a 5-6 membered heterocyclic group which has as hetero atom one of oxygen atom and nitrogen atom;

$R_6$ is an alkyl group of 1 to 12 carbon atoms, a phenethyl group which may be substituted with methyl, hydroxy or methoxy or a styryl group which may be substituted with methyl, hydroxy or methoxy and X is a group

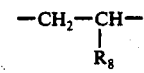

wherein $R_8$ is hydrogen, $C_1$-$C_{12}$ alkyl or phenyl; or $R_9$ is hydrogen atom or phenyl group and $R_{10}$ is a phenyl group which has one hydroxy group at the o- or p-position and 2-4 groups selected from the group consisting of $C_1$-$C_4$ alkyl, hydroxymethyl, a group

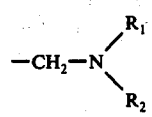

wherein $R_1$ and $R_2$ are as defined above, and a group

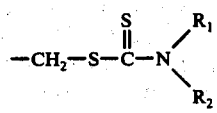

wherein $R_1$ and $R_2$ are as defined above, a group

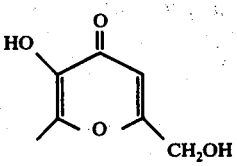

or a group

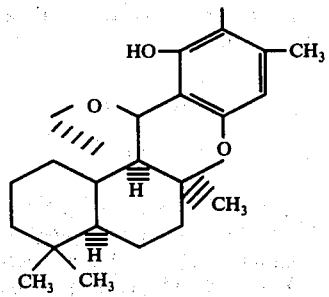

4. A composition according to claim 1, wherein the compound is 4-hydroxy-3,5-di-6-butylbenzyl 4-morpholinecarbodithioate.

5. A composition according to claim 1, wherein the compound is 2-oxocyclopentylmethyl 4-morpholinecarbodithioate.

6. A composition according to claim 1, wherein the compound is 2-oxocyclohexylmethyl 4-morpholinecarbodithioate.

7. A composition according to claim 1, wherein the compound is 2-(o-hydroxybenzoyl)ethyl 4-morpholinecarbodithioate.

8. A composition according to claim 1, wherein the compound is 2-(o-nitrobenzoyl)ethyl 4-morpholinecarbodithioate.

9. A composition according to claim 1, wherein the compound is 2-acetylethyl 4-morpholinecarbodithioate.

10. A composition according to claim 1, wherein the compound is 2-propionylethyl 4-morpholinecarbodithioate.

11. A composition according to claim 1, wherein the compound is 4-hydroxy-3,5-di-isopropylbenzyl 4-morpholinecarbodithioate.

12. A composition according to claim 1, wherein the compound is 4-hydroxy-3,5-di-t-butylbenzyl 4-morpholinecarbodithioate.

* * * * *

UNITED STATES PATENT AND TRADEMARK OFFICE
CERTIFICATE OF CORRECTION

PATENT NO. : 4,076,814

DATED : February 28, 1978

INVENTOR(S) : ISAO SEKI et al

It is certified that error appears in the above-identified patent and that said Letters Patent are hereby corrected as shown below:

Column 3, lines 1-13; Column 6, lines 55-64;
Column 8, lines 1-13; Column 30, lines 50-60 (Claim 1);
Column 31, lines 60-65 (Claim 2); and
Column 32, lines 60-65 (Claim 3):

in the formula, replace " 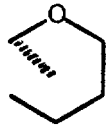 " with --- 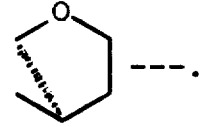 ---.

Column 3, line 45: replace "ect." with ---etc.---.

Column 5, line 7: replace "are" with ---as----.

Column 5, line 41, and Column 5, line 48: replace "curvative" with ---curative---.

Column 8, lines 15-16: replace "herinbelow" with ---hereinbelow---.

Column 8, lines 22-23: replace "1-piperidinecarbodthioate" with ---1-piperidinecarbodithioate---.

Column 9, line 39, at "(54)": after "ethyl", delete "b".

Column 9, lines 43-45, at "(58)": "58...dimethyldithiocarbonate" should be printed on a separate line.

UNITED STATES PATENT AND TRADEMARK OFFICE
CERTIFICATE OF CORRECTION

PATENT NO. : 4,076,814
DATED : February 28, 1978
INVENTOR(S) : ISAO SEKI et al

It is certified that error appears in the above-identified patent and that said Letters Patent are hereby corrected as shown below:

Column 10, line 13, at "(80)": replace "Acethylethyl" with ---Acetylethyl---.

Column 10, line 42, at "(101)": replace "4-morphonlinecarbodithioate" with ---4-morpholinecarbodithioate---.

Column 13, line 29, at "(215)": replace "3,5di..." with ---3,5-di...---.

Column 13, line 33, at "(217)": replace "butylbenzly" with ---butylbenzyl---.

Column 13, line 52, at "(226)": replace "piperazine-carbondithioate" with ---piperazinecarbodithioate---.

Column 14, line 8, at "(238)": "...methyl5-" should be ---...methyl-5- ---.

Column 14, line 10, at "(239)": after "-3-(", delete ";b".

Column 14, line 11, at "(239)": replace "metyl" with ---methyl---.

Column 14, line 19, at "(243)": replace "hydroxymetyl-benzyl" with ---hydroxymethylbenzyl---.

UNITED STATES PATENT AND TRADEMARK OFFICE
CERTIFICATE OF CORRECTION

PATENT NO. : 4,076,814
DATED : February 28, 1978
INVENTOR(S) : ISAO SEKI et al

It is certified that error appears in the above-identified patent and that said Letters Patent are hereby corrected as shown below:

Column 14, line 41, at "(253)": replace "piperzone" with ---piperazine---.

Column 15, line 28, at "(280)" and Column 16, line 1, at "(300)":
replace "moropholino" with ---morpholino---.

Column 16, line 24: replace "manely" with ---namely---.

Column 17, line 12: replace "absorpiton" with ---absorption---.

Column 17, line 18: replace "benezene" with ---benzene---.

Column 18, line 10: replace "demethyldithiocarbamate" with ---dimethyldithiocarbamate---.

Column 18, line 67: replace "Hydroxybenzoly" with ---Hydroxybenzoyl---.

Column 19, line 15: delete ";20" after "124.5".

Column 20, line 65: replace "2Acetyl" with ---2-Acetyl---.

Column 22, last line: replace "yimethyl" with ---ylmethyl---.

UNITED STATES PATENT AND TRADEMARK OFFICE
CERTIFICATE OF CORRECTION

PATENT NO. : 4,076,814
DATED : February 28, 1978
INVENTOR(S) : ISAO SEKI et al

It is certified that error appears in the above-identified patent and that said Letters Patent are hereby corrected as shown below:

Column 31, line 14 (Claim 2): replace "methyl hydroxy" with ---methyl, hydroxy---.

Column 32, line 7 (Claim 3): replace "oxoxcycloalkyl" with ---oxocycloalkyl---.

Signed and Sealed this

*Fifteenth* Day of *May 1979*

[SEAL]

Attest:

RUTH C. MASON
*Attesting Officer*

DONALD W. BANNER
*Commissioner of Patents and Trademarks*